United States Patent
Ezoe et al.

(10) Patent No.: US 12,303,241 B2
(45) Date of Patent: May 20, 2025

(54) SPHYGMOMANOMETER, BLOOD PRESSURE CALCULATION METHOD, AND COMPUTER-READABLE RECORDING MEDIUM

(71) Applicant: OMRON HEALTHCARE CO., LTD., Muko (JP)

(72) Inventors: Mika Ezoe, Kyoto (JP); Yukiya Sawanoi, Kyoto (JP); Shingo Yamashita, Kyoto (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 714 days.

(21) Appl. No.: 17/590,318

(22) Filed: Feb. 1, 2022

(65) Prior Publication Data

US 2022/0151503 A1    May 19, 2022

Related U.S. Application Data

(63) Continuation of application No. PCT/JP2020/029705, filed on Aug. 3, 2020.

(30) Foreign Application Priority Data

Aug. 15, 2019  (JP) .................................. 2019-149007
Oct. 28, 2019  (JP) .................................. 2019-195246

(51) Int. Cl.
*A61B 5/022*        (2006.01)
*A61B 5/00*         (2006.01)
(Continued)

(52) U.S. Cl.
CPC ...... *A61B 5/02225* (2013.01); *A61B 5/02141* (2013.01); *A61B 5/0235* (2013.01); *A61B 5/6824* (2013.01)

(58) Field of Classification Search
CPC ............ A61B 5/02225; A61B 5/02141; A61B 5/0235; A61B 5/021; A61B 5/022; A61B 5/0225; A61B 5/6824
See application file for complete search history.

(56) References Cited

U.S. PATENT DOCUMENTS

| | | | |
|---|---|---|---|
| 2006/0142663 A1 | 6/2006 | Sawanoi et al. | |
| 2017/0035366 A1* | 2/2017 | Kuwabara | A61B 5/743 |
| 2018/0192946 A1* | 7/2018 | Adachi | A61B 5/022 |

FOREIGN PATENT DOCUMENTS

| | | |
|---|---|---|
| CN | 109893110 A | 6/2019 |
| CN | 109893111 A | 6/2019 |

(Continued)

OTHER PUBLICATIONS

Translation of CN 109893111 (Year: 2019).*

(Continued)

*Primary Examiner* — Devin B Henson
(74) *Attorney, Agent, or Firm* — Oliff PLC (57) ABSTRACT

The present invention has a normal blood pressure measurement mode in which a blood pressure measurement is performed according to a blood pressure measurement instruction, and a nighttime blood pressure measurement mode in which a blood pressure measurement is automatically started according to a predetermined schedule. When being switched by an mode operation unit from the normal blood pressure measurement mode to the nighttime blood pressure measurement mode, an algorithm for blood pressure calculation by an oscillometric method is switched and set from an algorithm for a sitting position to an algorithm for a supine position. A blood pressure value is calculated using an algorithm currently set for the blood pressure calculation by the oscillometric method.

7 Claims, 8 Drawing Sheets

(51) Int. Cl.
    *A61B 5/021*     (2006.01)
    *A61B 5/0235*     (2006.01)

(56) References Cited

FOREIGN PATENT DOCUMENTS

| | | |
|---|---|---|
| JP | 863-234945 A | 9/1988 |
| JP | 2018-153240 A | 10/2018 |
| WO | 2011/055717 A1 | 5/2011 |
| WO | 2012/018029 A1 | 2/2012 |
| WO | 2018/168797 A1 | 9/2018 |

OTHER PUBLICATIONS

Jun. 19, 2024 Office Action issued in Chinese Patent Application No. 202080056723.7.
Sep. 24, 2020 Search Report issued in International Patent Application No. PCT/JP2020/029705.
Feb. 8, 2022 International Preliminary Report on Patentability issued in International Patent Application No. PCT/JP2020/029705.

* cited by examiner

SPHYGMOMANOMETER, BLOOD PRESSURE CALCULATION METHOD, AND COMPUTER-READABLE RECORDING MEDIUM

CROSS-REFERENCE TO RELATED APPLICATION

This application is based on an application No. 2019-149007 filed in Japan on Aug. 15, 2019, the entire content of which is hereby incorporated by reference.

TECHNICAL FIELD

The present invention relates to a sphygmomanometer, and more particularly to a sphygmomanometer having a normal blood pressure measurement mode and a nighttime (sleep) blood pressure measurement mode. The present invention also relates to a blood pressure calculation method of calculating a blood pressure by such a sphygmomanometer. The present invention also relates to a computer-readable recording medium storing a program for causing a computer to execute such a blood pressure calculation method.

BACKGROUND ART

Conventionally, as this type of sphygmomanometer, for example, Patent Literature 1 (WO 2018/168797 A) discloses a sphygmomanometer that switches a measurement posture determination condition between a normal blood pressure measurement mode and a nighttime blood pressure measurement mode in order to appropriately determine whether or not a measurement position of the sphygmomanometer is correct for each measurement posture of a sitting position and a supine position.

In addition, for example, Patent Literature 2 (JP 2018-153240 A) discloses a sphygmomanometer that corrects a blood pressure value using height information of the sphygmomanometer measured during measurement including sleeping.

SUMMARY OF INVENTION

Patent Literatures 1 and 2 also disclose applying these techniques to a wrist-type sphygmomanometer attached to a wrist (forearm). However, since the wrist-type sphygmomanometer has a high degree of freedom in position, there is a problem that processing of accurately measuring or determining the measurement posture while sleeping is low in stability.

Therefore, an object of the present invention is to provide a sphygmomanometer capable of stably and accurately calculating a blood pressure value in a sphygmomanometer having a normal blood pressure measurement mode and a nighttime (sleep) blood pressure measurement mode. Another object of the present invention is to provide a blood pressure calculation method capable of stably and accurately calculating a blood pressure by such a sphygmomanometer. Another object of the present invention is to provide a computer-readable recording medium storing a program for causing a computer to execute such a blood pressure calculation method.

In order to achieve the above object, a sphygmomanometer according to the present disclosure is a sphygmomanometer that temporarily presses a wrist as a measurement target site with a blood pressure measuring cuff, and performs blood pressure measurement by an oscillometric method, the sphygmomanometer comprising:

a measurement instruction input unit that inputs a blood pressure measurement instruction;

a mode operation unit that inputs an instruction to switch a mode between a normal blood pressure measurement mode in which the blood pressure measurement is performed according to the blood pressure measurement instruction input by the measurement instruction input unit and a nighttime blood pressure measurement mode in which the blood pressure measurement is automatically started according to a predetermined schedule;

an algorithm storage unit that stores an algorithm for a sitting position and an algorithm for a supine position as an algorithm for blood pressure calculation by the oscillometric method;

a first switching unit that switches and sets the algorithm for the blood pressure calculation by the oscillometric method from the algorithm for the sitting position to the algorithm for the supine position when being switched by the mode operation unit from the normal blood pressure measurement mode to the nighttime blood pressure measurement mode; and a blood pressure calculation unit that calculates a blood pressure value using an algorithm currently set for the blood pressure calculation by the oscillometric method based on a pressure of the blood pressure measuring cuff when the blood pressure measuring cuff is in a pressurization process or a depressurization process.

In the present specification, the "measurement instruction input unit" and the "mode operation unit" may be configured by, for example, switches provided in a main body of the sphygmomanometer, and may receive a switch-on by a user as an instruction, or may be configured by a communication unit that receives an instruction from a smartphone or the like existing outside the sphygmomanometer via wireless communication.

The "algorithm for the blood pressure calculation by the oscillometric method" means an algorithm that sets an envelope for a sequence of pulse wave amplitudes obtained from a cuff pressure when the blood pressure measuring cuff is in a pressurization process or a depressurization process, sets threshold levels (including a threshold level for systole and a threshold level for diastole) at a predetermined ratio with respect to a maximum value of the envelope, and calculates the cuff pressure at a time point when the envelope crosses the threshold levels as a maximum blood pressure (systolic blood pressure) and a minimum blood pressure (diastolic blood pressure), respectively. A difference between the algorithm for the sitting position and the algorithm for the supine position is typically expressed as a difference in the threshold levels (For example, a difference in ratio with respect to the maximum value of the envelope, or a plus or minus numerical value (offset value) with respect to a certain ratio).

The "currently set algorithm" means an algorithm set at the time of blood pressure calculation by the blood pressure calculation unit.

In another aspect, a blood pressure calculation method according to the present disclosure is a blood pressure calculation method for a sphygmomanometer that temporarily presses a wrist as a measurement target site with a blood pressure measuring cuff, and performs blood pressure measurement by an oscillometric method, wherein the sphygmomanometer includes:

a measurement instruction input unit configured to input a blood pressure measurement instruction;

a mode operation unit configured to input an instruction to switch a mode between a normal blood pressure measurement mode in which the blood pressure measurement is performed according to the blood pressure measurement instruction input by the measurement instruction input unit and a nighttime blood pressure measurement mode in which the blood pressure measurement is automatically started according to a predetermined schedule; and an algorithm storage unit that stores an algorithm for a sitting position and an algorithm for a supine position as an algorithm for blood pressure calculation by an oscillometric method, the blood pressure calculation method comprising:

switching and setting the algorithm for the blood pressure calculation by the oscillometric method from the algorithm for the sitting position to the algorithm for the supine position when being switched by the mode operation unit from the normal blood pressure measurement mode to the nighttime blood pressure measurement mode; and calculating a blood pressure value using an algorithm currently set for the blood pressure calculation by the oscillometric method based on a pressure of the blood pressure measuring cuff when the blood pressure measuring cuff is in a pressurization process or a depressurization process.

In yet another aspect, a computer-readable recording medium according to the present disclosure is a computer-readable recording medium non-transitorily storing a program for causing a computer to execute the above blood pressure calculation method.

BRIEF DESCRIPTION OF DRAWINGS

The present invention will become more fully understood from the detailed description given hereinbelow and the accompanying drawings which are given by way of illustration only, and thus are not limitative of the present invention, and wherein:

FIG. 7 includes sections (A), (B) and (C), which are hereinafter denoted as FIG. 7(A), FIG. 7(B) and FIG. 7(C), respectively.

DESCRIPTION OF EMBODIMENT

Hereinafter, embodiments of the present invention will be described in detail with reference to the drawings.

(Configuration of Sphygmomanometer)

Figure 1:
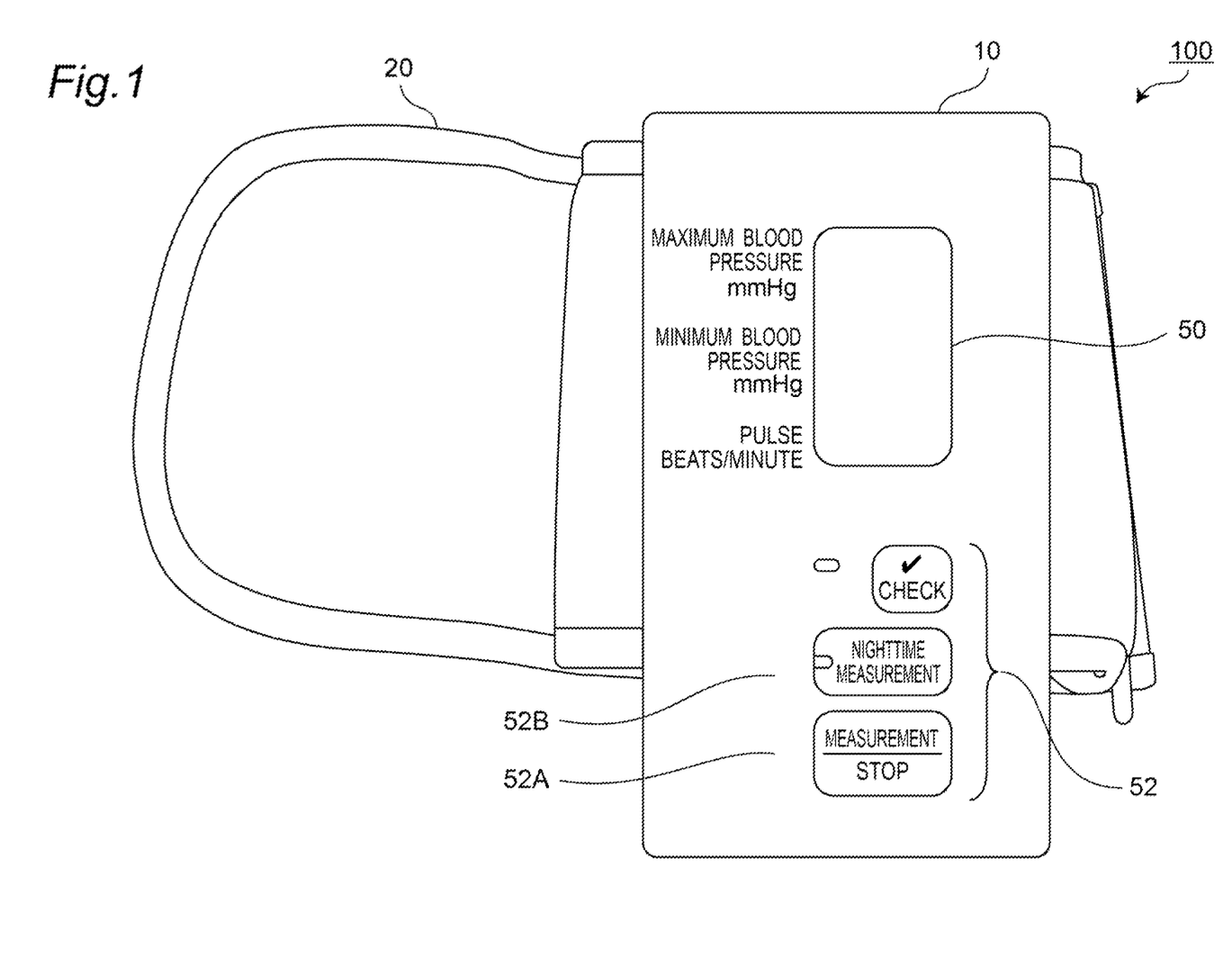
FIG. 1 is a view illustrating an appearance of a wrist-type sphygmomanometer according to an embodiment of the present invention.

FIG. 1 illustrates an appearance of a wrist-type sphygmomanometer 100 according to an embodiment of the present invention. The sphygmomanometer 100 roughly includes a blood pressure measuring cuff 20 to be attached to a left wrist 90 (see FIG. 3 described later) as a measurement target site, and a main body 10 integrally attached to the cuff 20.

The cuff 20 is a general one for a wrist-type sphygmomanometer, and has an elongated band shape so as to surround the left wrist 90 along a circumferential direction. The cuff 20 contains a fluid bag 22 (see FIG. 2) for compressing the left wrist 90. Note that, in order to always maintain the cuff 20 in an annular shape, a curler having appropriate flexibility may be provided in the cuff 20.

Figure 3:
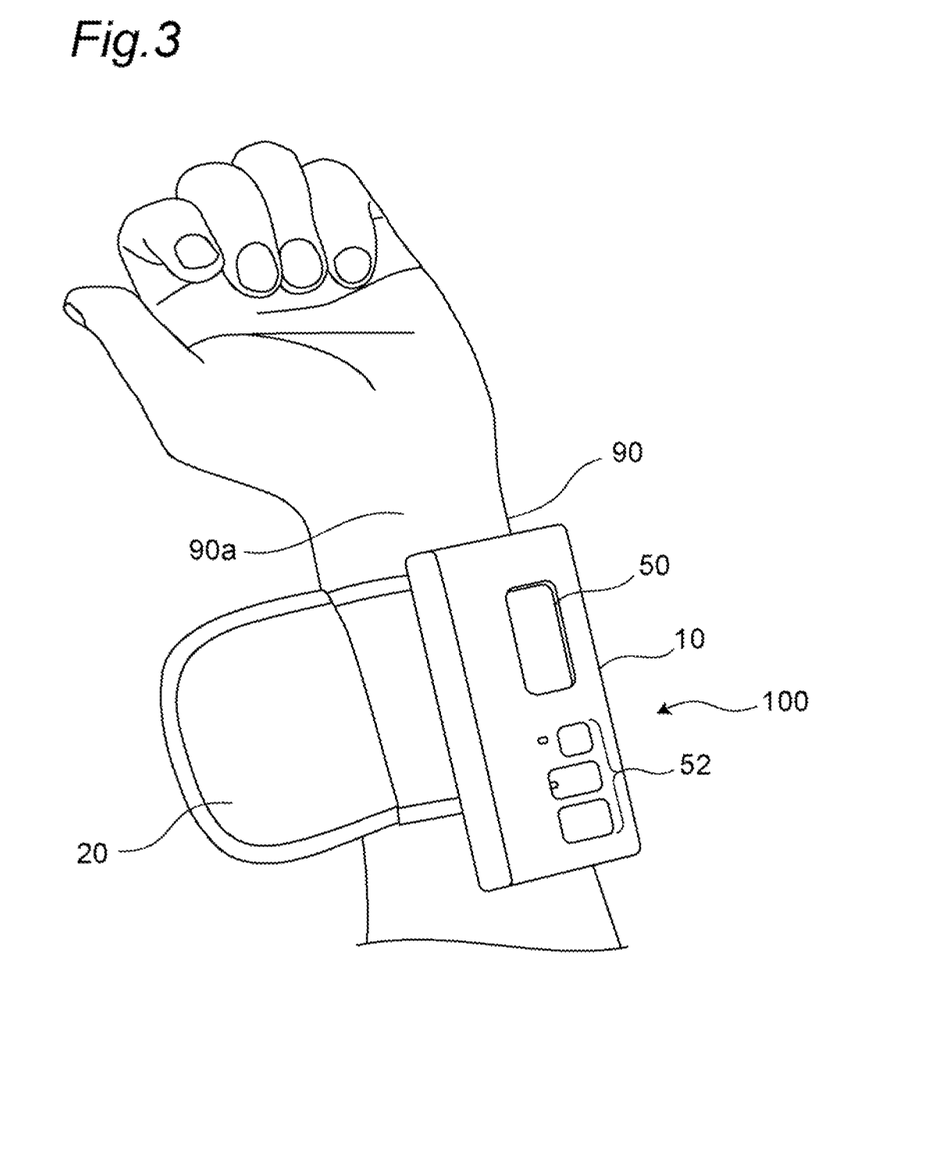
FIG. 3 is a view illustrating a mode in which the sphygmomanometer is attached to a left wrist as a measurement target site.

As illustrated in FIG. 3, the main body 10 is integrally attached to a substantially central portion in a longitudinal direction of the belt-shaped cuff 20. In this example, the portion to which the main body 10 is attached is supposed to correspond to a palmar surface (surface on a palm side) 90a of the left wrist 90 in a worn state.

The main body 10 has a flat substantially rectangular parallelepiped shape along an outer peripheral surface of the cuff 20. The main body 10 is formed to be small and thin so as not to interfere with the sleep of a user (in this example, a subject; the same applies hereinafter). Furthermore, corner portions of the main body 10 are rounded (The corners are rounded.).

As illustrated in FIG. 1, a display 50 forming a display screen, and an operation unit 52 for inputting an instruction from the user are provided on a surface (top surface) on a side farthest from the left wrist 90 among outer surfaces of the main body 10.

In this example, the display 50 is a liquid crystal display (LCD), and displays predetermined information according to a control signal from a central processing unit (CPU) 110 described later. In this example, maximum blood pressure (unit; mmHg), minimum blood pressure (unit; mmHg), and pulse (unit; beats per minute) are displayed. Note that the display 50 may be an organic electro luminescence (EL) display, or may include a light emitting diode (LED).

The operation unit 52 inputs an operation signal corresponding to an instruction from the user to the CPU 110 described later. In this example, the operation unit 52 includes a measurement switch 52A as a measurement instruction input unit for receiving a blood pressure measurement instruction from the user, and a nighttime measurement switch 52B as a mode operation unit for receiving an instruction to switch a mode between a normal blood pressure measurement mode and a nighttime blood pressure measurement mode. Here, the "normal blood pressure measurement mode" means a mode in which, when a blood pressure measurement instruction is input by the measurement switch 52A, blood pressure measurement is performed according to the blood pressure measurement instruction. The "nighttime blood pressure measurement mode" means a mode in which blood pressure measurement is automatically started according to a predetermined schedule so that the user can measure a blood pressure value during sleep. The predetermined schedule indicates, for example, a plan for measuring at regular time such as midnight 1:00, 2:00, or 3:00, a plan for measuring once every two hours after the nighttime measurement switch 52B is pressed, or the like.

Specifically, in this example, each of the measurement switch 52A and the nighttime measurement switch 52B is a momentary type (self-return type) switch, and is turned on only while being pushed down, and returns to an off state when being released.

When the measurement switch 52A is once pushed down while the sphygmomanometer 100 is in the normal blood pressure measurement mode, which means a blood pressure measurement instruction, the measurement target site (left wrist 90) is temporarily compressed by the cuff 20, and blood pressure measurement is executed by the oscillometric method. When the measurement switch 52A is pushed down again during the blood pressure measurement (for example, during pressurization of the cuff 20), it means an instruction to stop the blood pressure measurement, and the blood pressure measurement is immediately stopped.

When the nighttime measurement switch 52B is once pushed down while the sphygmomanometer 100 is in the normal blood pressure measurement mode, it means an instruction to transition to the nighttime blood pressure measurement mode, and the sphygmomanometer 100 transitions from the normal blood pressure measurement mode to the nighttime blood pressure measurement mode. In the nighttime blood pressure measurement mode, as described above, blood pressure measurement by the oscillometric method is automatically started according to the predetermined schedule. When the nighttime measurement switch 52B is pushed down again while the sphygmomanometer 100 is in the nighttime blood pressure measurement mode, it means an instruction to stop the nighttime blood pressure measurement mode, and the sphygmomanometer 100 transitions from the nighttime blood pressure measurement mode to the normal blood pressure measurement mode.

Even while the sphygmomanometer 100 is in the nighttime blood pressure measurement mode, the user may instruct blood pressure measurement by interrupting by pressing the measurement switch 52A separately from the predetermined schedule. At that time, in response to the interruption blood pressure measurement instruction, the measurement target site (left wrist 90) is temporarily compressed by the cuff 20, and blood pressure measurement is executed by the oscillometric method.

Figure 2:
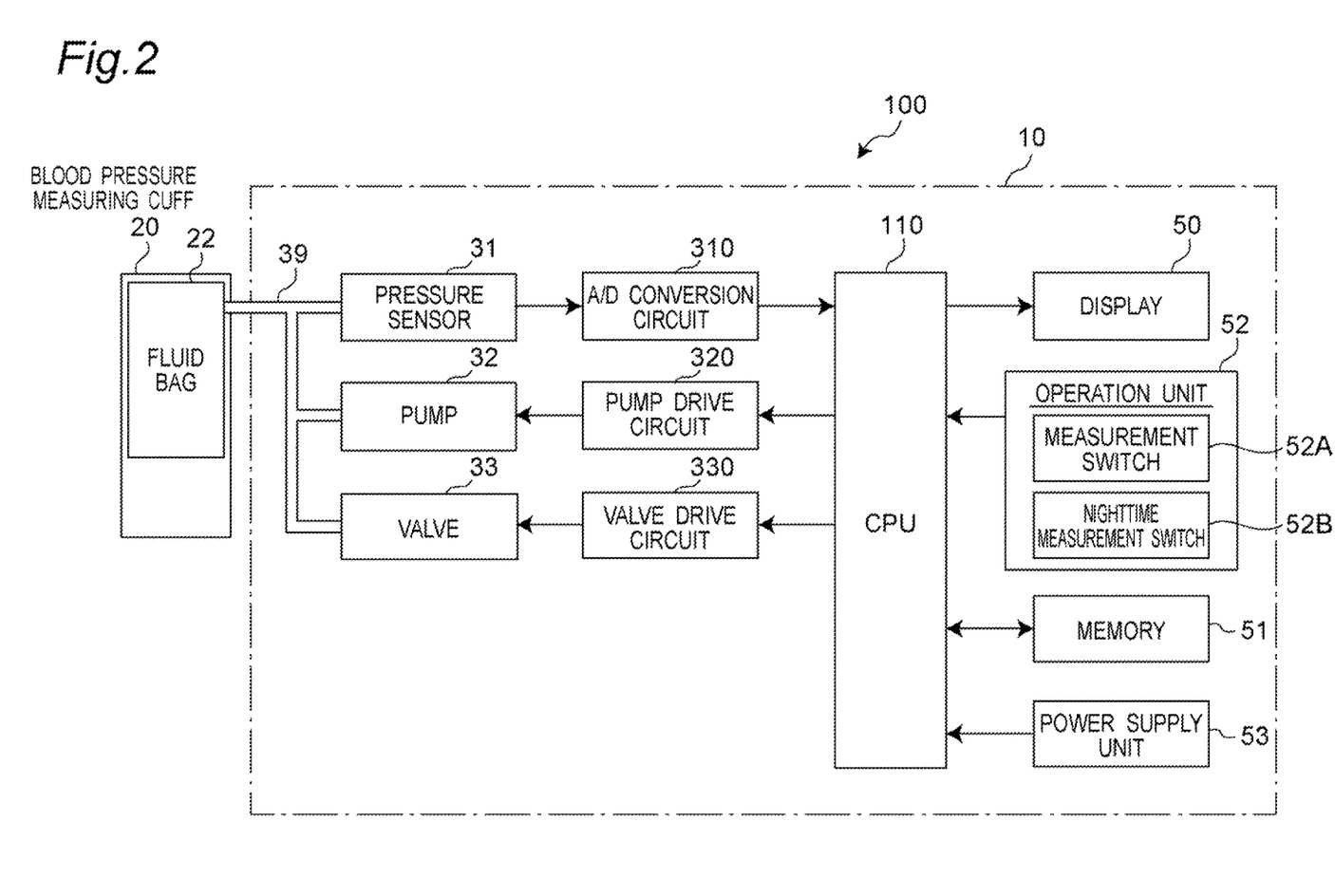
FIG. 2 is a diagram illustrating a block configuration of the sphygmomanometer.

FIG. 2 illustrates a block configuration of the sphygmomanometer 100.

As described above, the cuff 20 includes the fluid bag 22 for compressing the left wrist 90 as the measurement target site. The fluid bag 22 and the main body 10 are connected by an air pipe 39 so as to be capable of fluid communication with each other.

In addition to the display 50 and the operation unit 52 described above, the main body 10 is mounted with a CPU 110 as a control unit, a memory 51 as a storage unit, a power supply unit 53, a pressure sensor 31, a pump 32, and a valve 33. The main body 10 further includes an A/D conversion circuit 310 that converts an output of the pressure sensor 31 from an analog signal to a digital signal, a pump drive circuit 320 that drives the pump 32, and a valve drive circuit 330 that drives the valve 33. The pressure sensor 31, the pump 32, and the valve 33 are commonly connected to the fluid bag 22 through the air pipe 39 so as to be capable of fluid communication.

The memory 51 stores a program for controlling the sphygmomanometer 100, data used for controlling the sphygmomanometer 100, setting data for setting various functions of the sphygmomanometer 100, data of a measurement result of a blood pressure value, and the like. In addition, the memory 51 is used as a work memory or the like when a program is executed. In particular, in this example, the memory 51 serves as an algorithm storage unit, and stores an algorithm for a sitting position and an algorithm for a supine position as algorithms for blood pressure calculation by the oscillometric method.

Figure 4A:
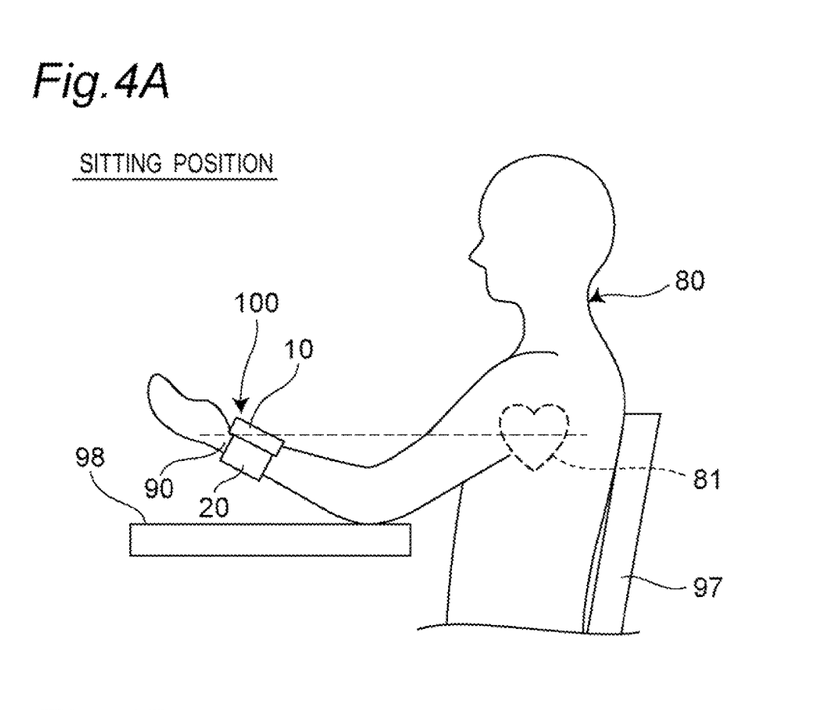
FIG. 4A is a view illustrating a sitting position as a measurement posture.
Figure 4B:
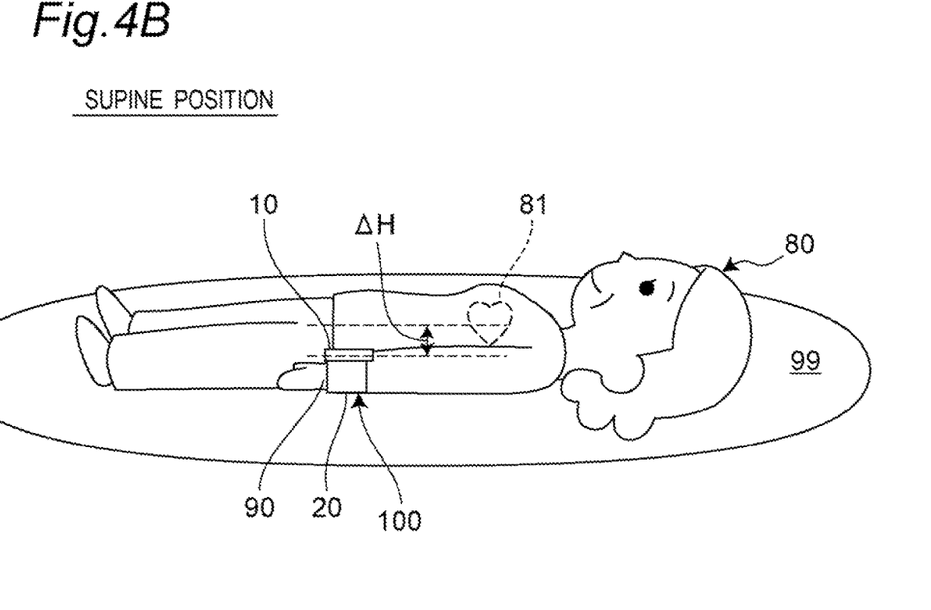
FIG. 4B is a view illustrating a supine position as a measurement posture.

Here, as illustrated in FIG. 4A, the "sitting position" means a posture in which the user 80 wearing the sphygmomanometer 100 on the left wrist 90 sits on a chair 97 or the like, and holds the left wrist 90 (and the sphygmomanometer 100) at a height level of a heart 81 by raising the left wrist 90 obliquely (hand is up, elbow is down) in front of a trunk with the left elbow attached to a table 98. This posture eliminates a height difference between the left wrist 90 and the heart 81 of the user 80, and thus is recommended to increase a blood pressure measurement accuracy. On the other hand, as illustrated in FIG. 4B, the "supine position" means a posture in which the user 80 wearing the sphygmomanometer 100 on the left wrist 90 lies on his/her back on a horizontal floor surface 99 or the like with the left elbow extended along the trunk. In this posture, a height difference ΔH between the left wrist 90 (and the sphygmomanometer 100) of the user 80 and the heart 81 occurs (the height of the heart 81 is higher than the height of the left wrist 90), so that the blood pressure measurement value deviates. In addition, since the left elbow is bent in the sitting position (FIG. 4A) while the left elbow is extended in the supine position (FIG. 4B), the blood pressure measurement value may be deviated due to bending and stretching of the left elbow. In order to eliminate such a deviation of the blood pressure measurement value in the supine position with respect to the blood pressure measurement value in the sitting position, it is preferable to change the blood pressure calculation algorithm in the case of measuring the blood pressure in the supine position with respect to the blood pressure calculation algorithm in the case of measuring the blood pressure in the sitting position. For this reason, in this example, the memory 51 stores the algorithm for the sitting position and the algorithm for the supine position as the algorithms for the blood pressure calculation by the oscillometric method. A specific method of calculating the blood pressure using the algorithm for the sitting position and the algorithm for the supine position will be described later.

The CPU 110 illustrated in FIG. 2 controls the entire operation of the sphygmomanometer 100. Specifically, the CPU 110 acts as a pressure control unit according to a program for controlling the sphygmomanometer 100 stored in the memory 51, and performs control to drive the pump 32 and the valve 33 according to an operation signal from the operation unit 52. Furthermore, the CPU 110 acts as a blood pressure calculation unit, calculates a blood pressure value using an algorithm for blood pressure calculation by the oscillometric method, and controls the display 50 and the memory 51.

In this example, the power supply unit 53 includes a secondary battery, and supplies power to every unit including the CPU 110, the pressure sensor 31, the pump 32, the valve 33, the display 50, the memory 51, the A/D conversion circuit 310, the pump drive circuit 320, and the valve drive circuit 330.

The pump 32 supplies air as a fluid to the fluid bag 22 through the air pipe 39 in order to pressurize a pressure (cuff pressure) in the fluid bag 22 included in the cuff 20. The valve 33 is opened and closed to discharge air in the fluid bag 22 through the air pipe 39 or to enclose air in the fluid bag 22 to control the cuff pressure. The pump drive circuit 320 drives the pump 32 based on a control signal given from the CPU 110. The valve drive circuit 330 opens and closes the valve 33 based on a control signal given from the CPU 110.

The pressure sensor 31 and the A/D conversion circuit 310 act as a pressure detection unit that detects the pressure of the cuff. The pressure sensor 31 is a piezoresistive pressure sensor in this example, and outputs the pressure (cuff pressure) in the fluid bag 22 contained in the cuff 20 through the air pipe 39 as an electric resistance due to the piezoresistive effect. The A/D conversion circuit 310 converts an output (electric resistance) of the pressure sensor 31 from an analog signal to a digital signal, and outputs the converted signal to the CPU 110. In this example, the CPU 110 acts as an oscillation circuit that oscillates at a frequency corresponding to the electric resistance from the pressure sensor 31, and acquires a signal indicating the cuff pressure according to the oscillation frequency.

(Blood Pressure Calculation Method)

Figure 5:
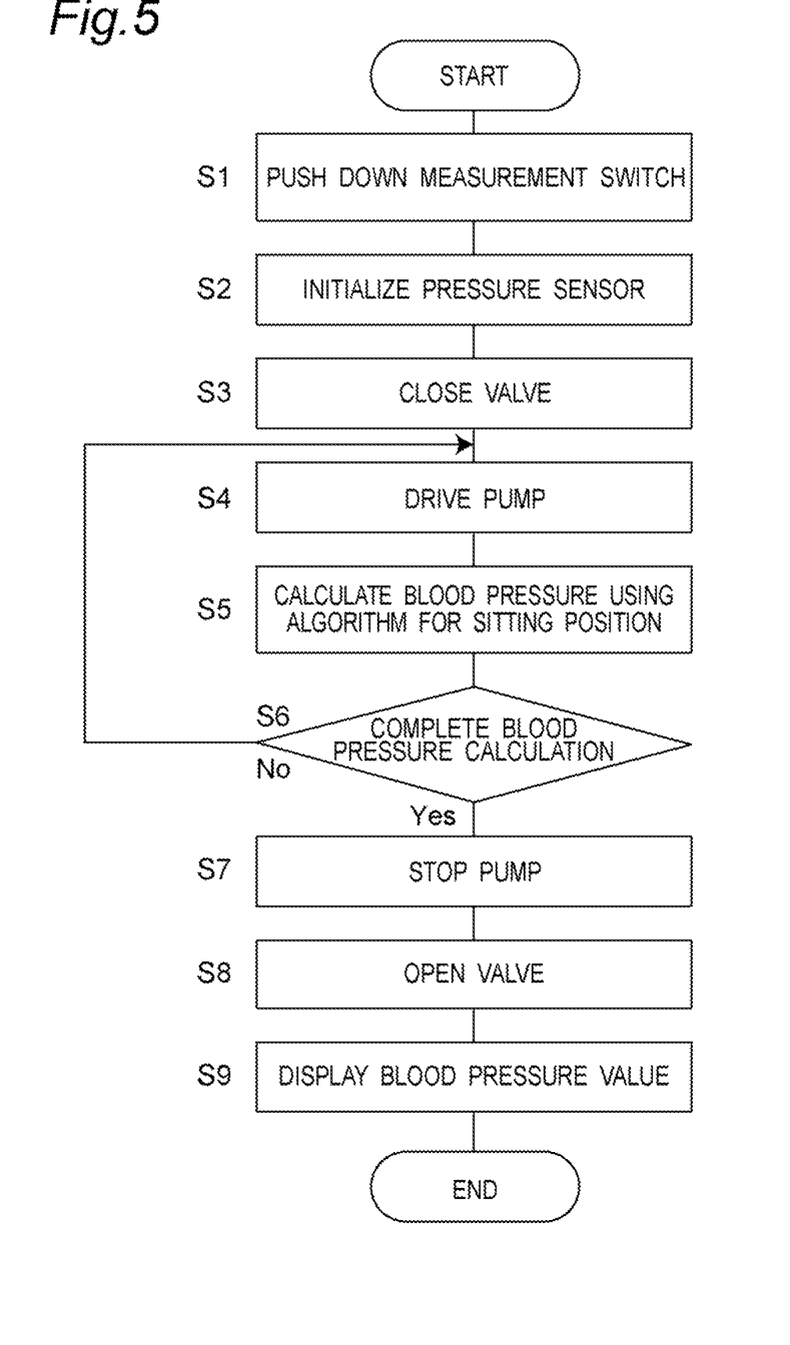
FIG. 5 is a diagram illustrating an operation flow when blood pressure measurement is performed in a normal blood pressure measurement mode by the sphygmomanometer.

FIG. 5 illustrates an operation flow when the user performs blood pressure measurement in the normal blood pressure measurement mode by the sphygmomanometer 100. In this example, when the measurement switch 52A is continuously pressed for, for example, three seconds or more in a power-off state, a power source is turned on, and the normal blood pressure measurement mode is set by default.

As illustrated in FIG. 4A, it is assumed that the user 80 wearing the sphygmomanometer 100 on the left wrist 90 is in a sitting posture.

In this state, as shown in step S1 of FIG. 5, when the user pushes down the measurement switch 52A provided on the main body 10 to input a blood pressure measurement instruction, the CPU 110 initializes the pressure sensor 31 (step S2). Specifically, the CPU 110 initializes a processing memory area, and performs a 0 mmHg adjustment (The atmospheric pressure is set to 0 mmHg.) of the pressure sensor 31 in a state where the pump 32 is turned off (stopped) and the valve 33 is opened.

Next, the CPU 110 closes the valve 33 via the valve drive circuit 330 (step S3), and then turns on (starts) the pump 32 via the pump drive circuit 320 to start pressurization of the cuff 20 (fluid bag 22) (step S4). At this time, the CPU 110 controls a pressurization speed of a cuff pressure PC, which is a pressure in the fluid bag 22, as illustrated in FIG. 7(A) based on the output of the pressure sensor 31 while supplying air from the pump 32 to the fluid bag 22 through the air pipe 39.

Figure 7:
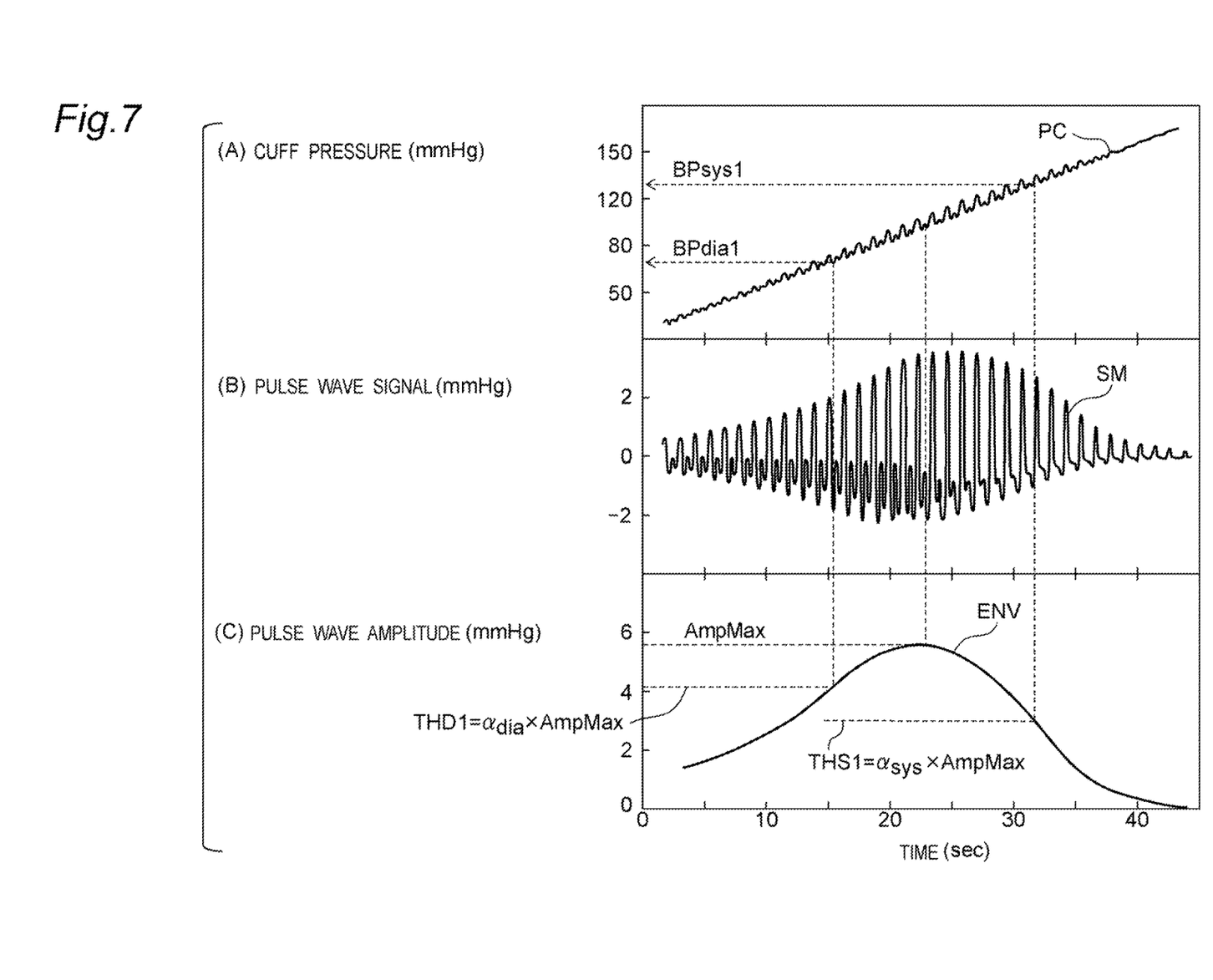
FIG. 7(A) is a graph illustrating a time course of a cuff pressure PC associated with blood pressure measurement.
FIG. 7(B) is a graph illustrating a time course of a pulse wave signal SM associated with the blood pressure measurement.
FIG. 7(C) is a graph illustrating an envelope ENV set for a sequence of pulse wave amplitudes formed by the pulse wave signals SM.

Next, in step S5 of FIG. 5, the CPU 110 acts as a blood pressure calculation unit, and attempts to calculate a blood pressure value (maximum blood pressure (systolic blood pressure) and minimum blood pressure (diastolic blood pressure)) using the algorithm for the sitting position stored in the memory 51 on the basis of a pulse wave signal SM (fluctuation component due to a pulse wave included in the output of the pressure sensor 31) acquired at this time (see FIG. 7(B)).

At this time, when the blood pressure value cannot be calculated yet due to lack of data (No in step S6), the processing of steps S4 to S6 is repeated unless the cuff pressure PC reaches an upper limit pressure (For safety, for example, 300 mmHg is predetermined.).

Here, the CPU 110 calculates the blood pressure value as follows. That is, an envelope ENV as illustrated in FIG. 7(C) is set for a sequence of pulse wave amplitudes (peak-to-peak) formed by the pulse wave signals SM illustrated in FIG. 7(B) obtained from the cuff pressure PC when the cuff 20 is in the pressurization process. At the same time, two threshold levels THD1 and THS1 of ratios $\alpha_{dia}$ and $\alpha_{sys}$ predetermined for the sitting position are set with respect to a maximum value AmpMax of the envelope ENV. THD1 is a threshold level for a diastolic blood pressure, and is set as THD1=$\alpha_{dia}\times$ AmpMax. In addition, THS1 is a threshold level for a systolic blood pressure, and is set as THS1=$\alpha_{sys}\times$ AmpMax. As an example, $\alpha_{dia}$=0.75 and $\alpha_{sys}$=0.4 (That is, THD1=0.75× AmpMax is set, and THS1=0.4× AmpMax is set.). Then, as illustrated in FIG. 7(A), the cuff pressures PC when the envelope ENV crosses the threshold levels THD1 and THS1 are calculated as the minimum blood pressure (diastolic blood pressure) BPdia1 and the maximum blood pressure (systolic blood pressure) BPsys1, respectively.

When the blood pressure value can be calculated in this manner (Yes in step S6), the CPU 110 turns off the pump 32 (step S7), opens the valve 33 (step S8), and performs control to exhaust the air in the cuff 20 (fluid bag 22).

Thereafter, the CPU 110 displays the calculated blood pressure value on the display 50 (step S9), and performs control to store the blood pressure value in the memory 51.

Figure 6:
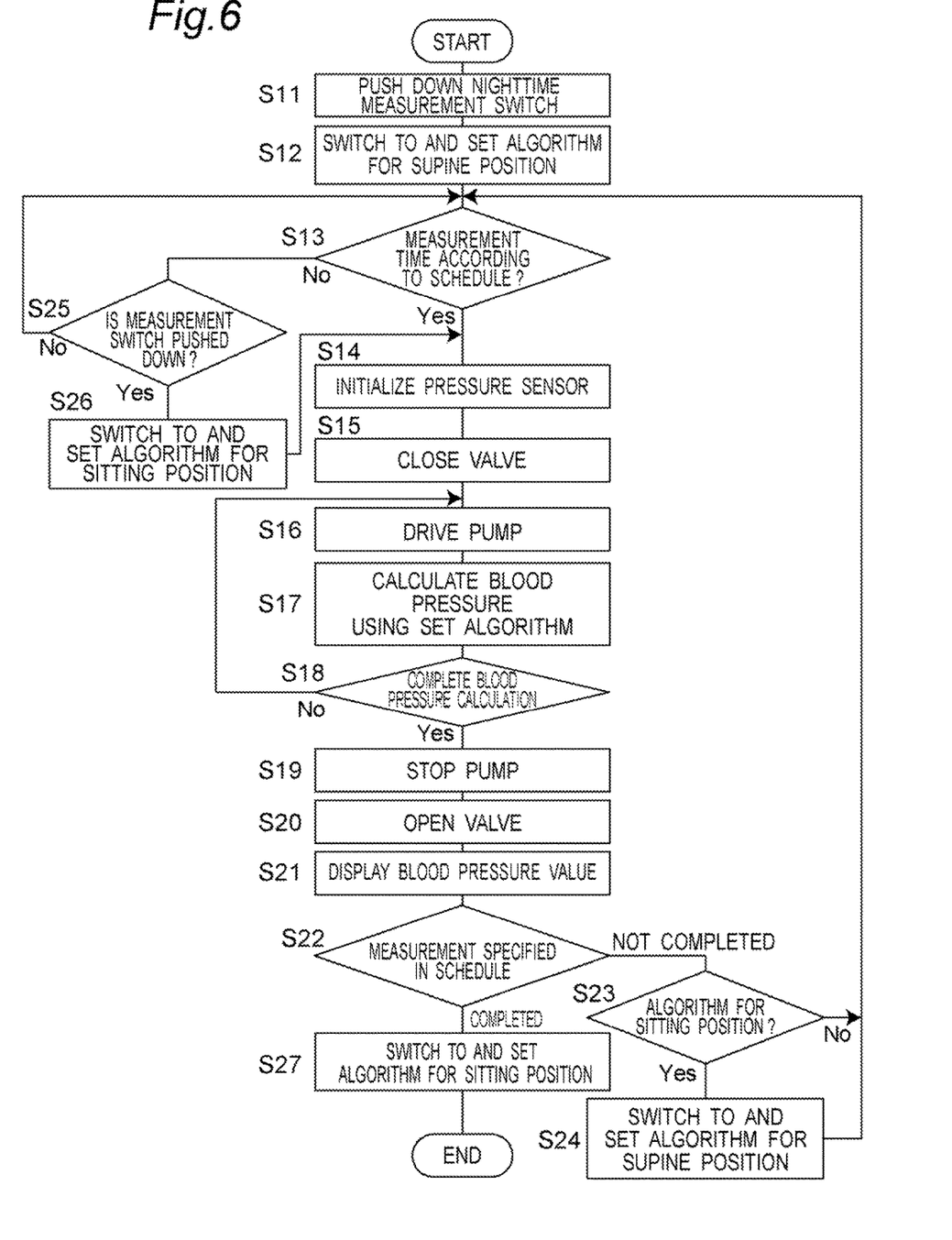
FIG. 6 is a diagram illustrating an operation flow when blood pressure measurement is performed in a nighttime blood pressure measurement mode by the sphygmomanometer.

FIG. 6 illustrates an operation flow when the user performs blood pressure measurement in the nighttime blood pressure measurement mode by the sphygmomanometer 100. At the start of this flow, the sphygmomanometer 100 is assumed to be in the normal blood pressure measurement mode.

As shown in step S11 of FIG. 6, when the user pushes down the nighttime measurement switch 52B provided on the main body 10, the sphygmomanometer 100 transitions from the normal blood pressure measurement mode to the nighttime blood pressure measurement mode. In this example, in the nighttime blood pressure measurement mode, it is assumed that a schedule of measuring once every two hours, for example, until 7:00 am after the nighttime measurement switch 52B is pressed is determined. Note that the present invention is not limited to this schedule, and a schedule for measuring on time such as 1:00 am, 2:00 am, and 3:00 am, for example, until 7:00 am from the time when the nighttime measurement switch 52B is pressed may be set.

With the transition to the nighttime blood pressure measurement mode, as described in step S12, the CPU 110 acts as a first switching unit, and switches and sets the algorithm for the blood pressure calculation by the oscillometric method from the algorithm for the sitting position to the algorithm for the supine position.

Figure 8:
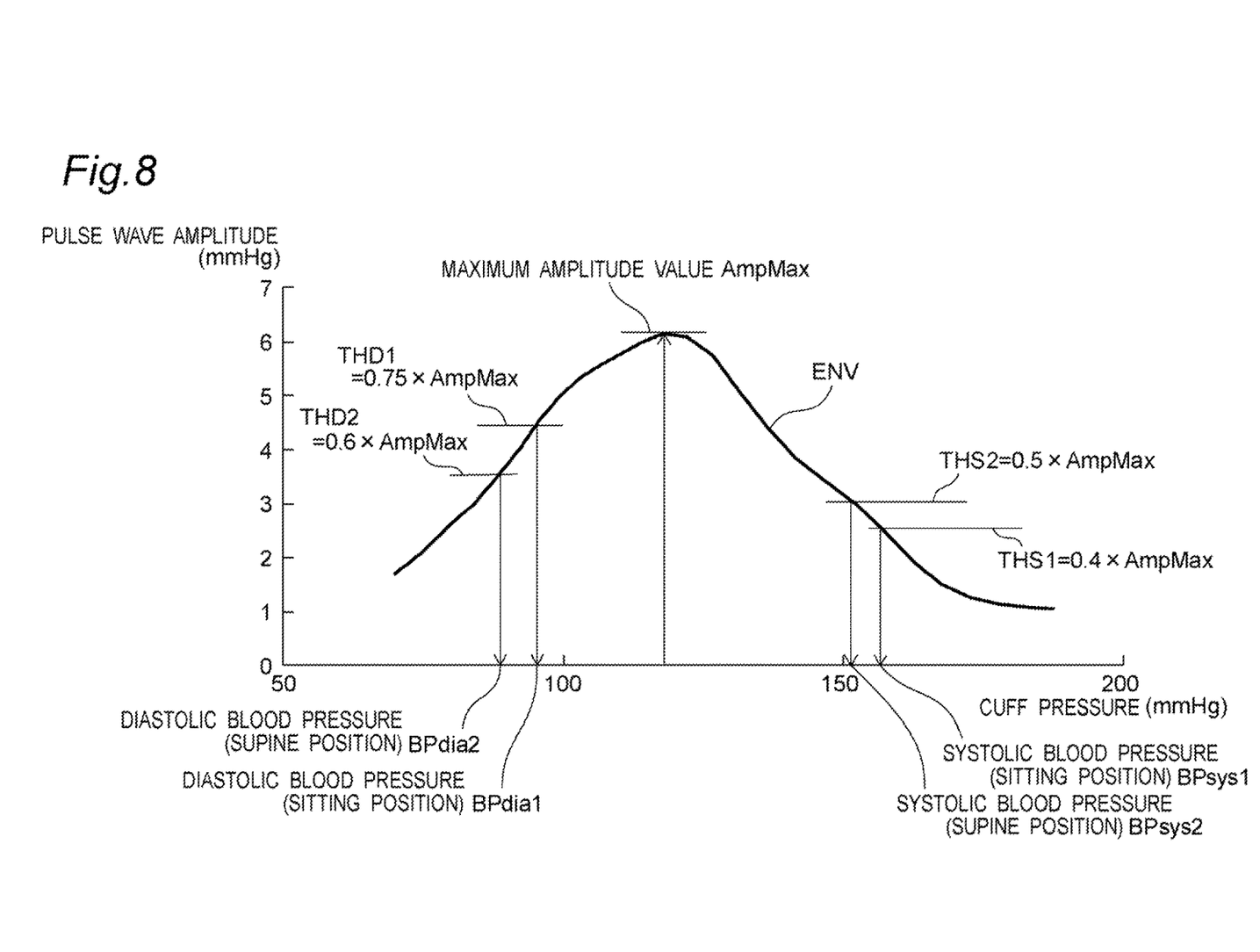
FIG. 8 is a graph for explaining how to calculate a blood pressure in the nighttime blood pressure measurement mode.

Specifically, as illustrated in FIG. 8, the threshold level for the diastolic blood pressure is set by switching from THD1 to THD2, and the threshold level for the systolic blood pressure is set by switching from THS1 to THS2. Here, THD2=0.6× AmpMax is set, and THS2=0.5× AmpMax is set. This corresponds to changing the ratio $\alpha_{dia}$ of the envelope ENV to the maximum value AmpMax from 0.75 for the sitting position to 0.6 for the supine position, and changing the ratio $\alpha_{sys}$ of the envelope ENV to the maximum value AmpMax from 0.4 for the sitting position to 0.5 for the supine position. The change of the ratios $\alpha_{dia}$ and $\alpha_{sys}$ is for eliminating the deviation of the blood pressure measurement value in the supine position (FIG. 4B) with respect to the blood pressure measurement value in the sitting position (FIG. 4A).

Note that the memory 51 desirably includes a flag indicating a currently set algorithm out of the algorithm for the sitting position and the algorithm for the supine position. In that case, the CPU 110 can easily recognize the currently set algorithm by referring to the flag.

Next, as shown in step S13 of FIG. 6, the CPU 110 determines whether or not it is the measurement time specified in the schedule (of the nighttime blood pressure measurement mode). If it is not the measurement time specified in the schedule (No in step S13), unless the measurement switch 52A is pushed down, the CPU 110 waits for the measurement time specified in the schedule (No in step S25).

When the measurement time specified in the schedule is reached (Yes in step S13), the CPU 110 starts blood pressure measurement same as in steps S2 to S4 in FIG. 5 as shown in steps S14 to S16 in FIG. 6. That is, the CPU 110 first initializes the pressure sensor 31 (step S14).

Next, the CPU 110 closes the valve 33 via the valve drive circuit 330 (step S15), and then turns on (starts) the pump 32 via the pump drive circuit 320 to start pressurization of the cuff 20 (fluid bag 22) (step S16). At this time, the CPU 110 controls a pressurization speed of the cuff pressure PC in the same manner as illustrated in FIG. 7(A).

Next, in step S17 of FIG. 6, the CPU 110 acts as a blood pressure calculation unit, and attempts to calculate a blood pressure value (maximum blood pressure (systolic blood pressure) and minimum blood pressure (diastolic blood pressure)) using a currently set algorithm (at this point, the algorithm for the supine position) based on the pulse wave signal SM (fluctuation component due to the pulse wave included in the output of the pressure sensor 31) acquired at this time (similar to that illustrated in FIG. 7(B)).

At this time, when the blood pressure value cannot be calculated yet due to lack of data (No in step S18), the processing of steps S16 to S18 is repeated unless the cuff pressure PC reaches an upper limit pressure (For safety, for example, 300 mmHg is predetermined.).

Here, the CPU 110 calculates the blood pressure value as follows. That is, the envelope ENV (similar to that illustrated in FIG. 7(C)) as illustrated in FIG. 8 is set for a sequence of the pulse wave amplitudes (peak-to-peak) formed by the pulse wave signals SM obtained from the cuff pressure PC when the cuff 20 is in the pressurization process. Then, the cuff pressures PC at the time when the envelope ENV crosses the currently set threshold levels THD2 (=0.6×AmpMax) and THS2 (=0.5×AmpMax) for the supine position are calculated as the minimum blood pressure (diastolic blood pressure) BPdia2 and the maximum blood pressure (systolic blood pressure) BPsys2, respectively.

In the nighttime blood pressure measurement mode, it is usually expected that the user is in a supine position. Therefore, by using the algorithm for the supine position, the blood pressure values (the maximum blood pressure and the minimum blood pressure) can be stably and accurately calculated.

When the blood pressure value can be calculated in this manner (Yes in step S18), the CPU 110 turns off the pump 32 (step S19), opens the valve 33 (step S20), and performs control to discharge the air in the cuff 20 (fluid bag 22).

Thereafter, the CPU 110 displays the calculated blood pressure value on the display 50 (step S21), and performs control to store the blood pressure value in the memory 51.

When one blood pressure measurement specified in the schedule is completed in this manner, in step S22, the CPU 110 determines whether or not all the blood pressure measurements specified in the schedule are completed. Here, as long as the blood pressure measurement is still scheduled according to the schedule ("Not Completed" in step S22), the currently set algorithm is the algorithm for the supine position (No in step S23), and thus the process directly returns to step S13. Then, the CPU 110 waits for the next measurement time specified in the schedule (No in step S13, No in step S25).

When the next measurement time specified in the schedule is reached (Yes in step S13), the CPU 110 repeats the processing in steps S14 to S21. Furthermore, in step S22, the CPU 110 determines whether or not all the blood pressure measurements specified in the schedule are completed, and as long as the blood pressure measurement is still scheduled according to the schedule ("Not Completed" in step S22), the process directly returns to step S13 (No in step S23). Then, the CPU 110 waits for the next measurement time specified in the schedule (No in step S13, No in step S25).

Even while the sphygmomanometer 100 is in the nighttime blood pressure measurement mode, the user may instruct blood pressure measurement by interrupting by pushing down the measurement switch 52A separately from the predetermined schedule (Yes in step S25). At this time, the user is expected to be in a sitting position rather than a supine position. Therefore, the CPU 110 acts as a second switching unit, and switches and sets the algorithm for the blood pressure calculation by the oscillometric method from the algorithm for the supine position to the algorithm for the sitting position (step S26).

Subsequently, as shown in steps S14 to S16, the CPU 110 starts blood pressure measurement according to the interruption blood pressure measurement instruction. That is, the CPU 110 first initializes the pressure sensor 31 (step S14).

Next, the CPU 110 closes the valve 33 via the valve drive circuit 330 (step S15), and then turns on (starts) the pump 32 via the pump drive circuit 320 to start pressurization of the cuff 20 (fluid bag 22) (step S16). At this time, the CPU 110 controls a pressurization speed of the cuff pressure PC in the same manner as illustrated in FIG. 7(A).

Next, in step S17 of FIG. 6, the CPU 110 acts as a blood pressure calculation unit, and attempts to calculate a blood pressure value (maximum blood pressure (systolic blood pressure) and minimum blood pressure (diastolic blood pressure)) using a currently set algorithm (at this point, the algorithm for the sitting position) based on the pulse wave signal SM (fluctuation component due to the pulse wave included in the output of the pressure sensor 31) acquired at this time (similar to that illustrated in FIG. 7(B)).

At this time, when the blood pressure value cannot be calculated yet due to lack of data (No in step S18), the processing of steps S16 to S18 is repeated unless the cuff pressure PC reaches an upper limit pressure (For safety, for example, 300 mmHg is predetermined.).

Here, the CPU 110 calculates the blood pressure value as follows. That is, the envelope ENV as illustrated in FIG. 8 is set for a sequence of the pulse wave amplitudes (peak-to-peak) formed by the pulse wave signals SM obtained from the cuff pressure PC when the cuff 20 is in the pressurizing process. Then, the cuff pressures PC at the time when the envelope ENV crosses the currently set threshold levels THD1 (=0.75×AmpMax) and THS1 (=0.4×AmpMax) for the sitting position are calculated as the minimum blood pressure (diastolic blood pressure) BPdia1 and the maximum blood pressure (systolic blood pressure) BPsys1, respectively.

When the blood pressure measurement is instructed by pushing down the measurement switch 52A (Yes in step S25), the user is expected to be in the sitting position rather than the supine position. Therefore, by using the algorithm for the sitting position, the blood pressure values (the maximum blood pressure and the minimum blood pressure) can be stably and accurately calculated.

When the blood pressure value can be calculated in this manner (Yes in step S18), the CPU 110 turns off the pump 32 (step S19), opens the valve 33 (step S20), and performs control to discharge the air in the cuff 20 (fluid bag 22).

Thereafter, the CPU 110 displays the calculated blood pressure value on the display 50 (step S21), and performs control to store the blood pressure value in the memory 51.

When the blood pressure measurement according to the interruption blood pressure measurement instruction is completed in this manner, in step S22, the CPU 110 determines whether or not all the blood pressure measurements specified in the schedule are completed. Here, it is assumed that the blood pressure measurement is still scheduled according to the schedule ("Not Completed" in step S22). Since the currently set algorithm is the algorithm for the sitting position (Yes in step S23), the CPU 110 acts as a third switching unit, and switches and sets the algorithm for the blood pressure calculation by the oscillometric method from the algorithm for the sitting position to the algorithm for the supine position (step S24). Thereafter, the process returns to step S13. Then, the CPU 110 waits for the next measurement time specified in the schedule (No in step S13, No in step S25).

When the next measurement time specified in the schedule is reached (Yes in step S13), the CPU 110 repeats the processing in steps S14 to S21. In this way, even after the blood pressure measurement according to the interruption blood pressure measurement instruction is completed, the blood pressure measurement is automatically started according to the schedule. At that time, in step S18, the CPU 110 calculates, as a blood pressure calculation unit, the minimum blood pressure (diastolic blood pressure) BPdia2 and the maximum blood pressure (systolic blood pressure) BPsys2 using the algorithm for the supine position.

In the nighttime blood pressure measurement mode, as described above, it is usually expected that the user is in the supine position. Therefore, after the blood pressure measurement according to the blood pressure measurement instruction of the interruption is completed, the blood pressure values (maximum blood pressure and minimum blood pressure) can be stably and accurately calculated by using the algorithm for the supine position.

In this way, when all the blood pressure measurements specified in the schedule are completed ("Completed" in step S22), the CPU 110 acts as a fourth switching unit, and switches and sets the algorithm for the blood pressure calculation by the oscillometric method from the algorithm for the supine position to the algorithm for the sitting position (step S27). Then, the nighttime blood pressure measurement mode ends.

As a result, when the normal blood pressure measurement mode is started by default after the end of the nighttime blood pressure measurement mode, for example, in step S5 of FIG. 5, the CPU 110 can calculate, as the blood pressure calculation unit, the blood pressure value using the algorithm for the sitting position for the blood pressure calculation by the oscillometric method. Therefore, the blood pressure calculation in the normal blood pressure measurement mode can be correctly executed.

As is clear from the above, according to the sphygmomanometer 100, the blood pressure value can be stably and accurately calculated when the blood pressure measurement according to the interruption blood pressure measurement instruction is performed in the nighttime blood pressure measurement mode separately from the predetermined schedule.

Furthermore, since the sphygmomanometer 100 is of a type that presses a wrist (In the above example, the left wrist 90 is used, but a right wrist may be used.) as a measurement target site, it is expected that the sphygmomanometer is less likely to disturb the sleep of the user (subject) than a type that presses an upper arm (Imai et al., "Development and evaluation of a home nocturnal blood pressure monitoring system using a wrist-cuff device", Blood Pressure Monitoring 2018, 23, P318-326). Therefore, the sphygmomanometer 100 is suitable for the nighttime blood pressure measurement.

In addition, since the sphygmomanometer 100 is integrally and compactly configured as a wrist-type sphygmomanometer, handling by the user becomes convenient.

Modified Example

In the above-described embodiment, in the operation flow of the nighttime blood pressure measurement mode of the sphygmomanometer 100 (FIG. 6), the measurement switch 52A is pushed down to determine whether or not a blood pressure measurement instruction has been issued by interruption (step S25), and the CPU 110 serves as the second switching unit to switch and set the algorithm for the blood pressure calculation by the oscillometric method from the algorithm for the supine position to the algorithm for the sitting position (step S26). However, the present invention is not limited to this, and these processing (Steps S25 and S26) may be omitted. In this case, the processing of determining whether or not the currently set algorithm is the algorithm for the sitting position (step S23), and the processing of switching and setting the algorithm for the blood pressure calculation by the oscillometric method from the algorithm for the sitting position to the algorithm for the supine position by the CPU 110 serving as the third switching unit (step S24) can be omitted together. Thus, the operation flow (FIG. 6) of the nighttime blood pressure measurement mode can be simplified.

In addition, in the above-described embodiment, in the operation flow of the nighttime blood pressure measurement mode of the sphygmomanometer 100 (FIG. 6), after all the blood pressure measurements specified in the schedule are completed ("Completed" in step S22), the CPU 110 serves as the fourth switching unit, and the processing of switching and setting the algorithm for the blood pressure calculation by the oscillometric method from the algorithm for the supine position to the algorithm for the sitting position (step S27) is included. However, the present invention is not limited to this, and the processing (step S27) may be omitted. As a result, the operation flow (FIG. 6) of the nighttime blood pressure measurement mode can be simplified. In this case, the user temporarily turns off the power of the sphygmomanometer 100 after the end of the nighttime blood pressure measurement (In this example, when the measurement switch 52A is continuously pressed for, for example, three seconds or more in a power-on state, the power is turned off.). When the user wants to perform the nighttime blood pressure measurement again, the sphygmomanometer 100 is powered on (As described above, when the measurement switch 52A is continuously pressed for, for example, three seconds or more in a power-off state, the power is turned on.), the normal blood pressure measurement mode (algorithm for the sitting position) is set by default, and then the nighttime measurement switch 52B is pushed down to set the nighttime blood pressure measurement mode (algorithm for the supine position).

In the above-described embodiment, the blood pressure is calculated in the pressurization process of the cuff 20 (fluid bag 22), but the present invention is not limited to this. The blood pressure may be calculated in the depressurization process of the cuff 20.

Furthermore, in the above-described embodiment, the measurement switch 52A and the nighttime measurement switch 52B provided in the main body 10 are provided as the measurement instruction input unit and the mode operation unit, respectively, but the present invention is not limited to this. The measurement instruction input unit and the mode operation unit may be configured by, for example, a communication unit that receives an instruction from a smartphone or the like existing outside the sphygmomanometer 100 via wireless communication.

Further, in the above embodiment, the main body 10 is provided integrally with the cuff 20, but the present invention is not limited to this. The main body 10 may be configured as a separate body from the cuff 20, and may be connected to the cuff 20 (fluid bag 22) through a flexible air tube so as to be capable of fluid communication.

The above-described blood pressure calculation method (in particular, the operation flow of FIG. 6) may be recorded as software (a computer program) on a non-transitory recording medium capable of storing data, such as a compact disc (CD), a digital universal disc (DVD), or a flash memory. By installing software recorded on such a recording medium in a substantial computer device such as a personal computer, a personal digital assistant (PDA), or a smartphone, the computer device can be caused to execute the above-described blood pressure calculation method.

As described above, a sphygmomanometer according to the present disclosure is a sphygmomanometer that temporarily presses a wrist as a measurement target site with a blood pressure measuring cuff, and performs blood pressure measurement by an oscillometric method, the sphygmomanometer comprising:
  a measurement instruction input unit that inputs a blood pressure measurement instruction;
  a mode operation unit that inputs an instruction to switch a mode between a normal blood pressure measurement mode in which the blood pressure measurement is performed according to the blood pressure measurement instruction input by the measurement instruction input unit and a nighttime blood pressure measurement mode in which the blood pressure measurement is automatically started according to a predetermined schedule;
  an algorithm storage unit that stores an algorithm for a sitting position and an algorithm for a supine position as an algorithm for blood pressure calculation by the oscillometric method;
  a first switching unit that switches and sets the algorithm for the blood pressure calculation by the oscillometric method from the algorithm for the sitting position to the algorithm for the supine position when being switched by the mode operation unit from the normal blood pressure measurement mode to the nighttime blood pressure measurement mode; and
  a blood pressure calculation unit that calculates a blood pressure value using an algorithm currently set for the blood pressure calculation by the oscillometric method based on a pressure of the blood pressure measuring cuff when the blood pressure measuring cuff is in a pressurization process or a depressurization process.

In the present specification, the "measurement instruction input unit" and the "mode operation unit" may be configured by, for example, switches provided in a main body of the sphygmomanometer, and may receive a switch-on by a user as an instruction, or may be configured by a communication unit that receives an instruction from a smartphone or the like existing outside the sphygmomanometer via wireless communication.

The "algorithm for the blood pressure calculation by the oscillometric method" means an algorithm that sets an envelope for a sequence of pulse wave amplitudes obtained from a cuff pressure when the blood pressure measuring cuff is in a pressurization process or a depressurization process, sets threshold levels (including a threshold level for systole and a threshold level for diastole) at a predetermined ratio with respect to a maximum value of the envelope, and calculates the cuff pressure at a time point when the envelope crosses the threshold levels as a maximum blood pressure (systolic blood pressure) and a minimum blood pressure (diastolic blood pressure), respectively. A difference between the algorithm for the sitting position and the algorithm for the supine position is typically expressed as a difference in the threshold levels (For example, a difference in ratio with respect to the maximum value of the envelope, or a plus or minus numerical value (offset value) with respect to a certain ratio).

The "currently set algorithm" means an algorithm set at the time of blood pressure calculation by the blood pressure calculation unit.

In the sphygmomanometer of the present disclosure, the algorithm storage unit stores the algorithm for the sitting position and the algorithm for the supine position as the algorithm for the blood pressure calculation by the oscillometric method. When being switched by the mode operation unit from the normal blood pressure measurement mode to the nighttime blood pressure measurement mode, the first switching unit switches and sets the algorithm for the blood pressure calculation by the oscillometric method from the algorithm for the sitting position to the algorithm for the supine position. In the nighttime blood pressure measurement mode, blood pressure measurement is automatically started according to the predetermined schedule. That is, a measurement target site is temporarily pressed by the blood pressure measuring cuff according to the predetermined schedule. When the blood pressure measuring cuff is in the pressurization process or the depressurization process, the blood pressure calculation unit calculates a blood pressure value using an algorithm (at this point, the algorithm for the supine position) currently set for the blood pressure calculation by the oscillometric method based on a pressure of the blood pressure measuring cuff. In the nighttime blood pressure measurement mode, a subject is usually expected to be in a supine position. Therefore, by using the algorithm for the supine position, blood pressure values (maximum blood pressure and minimum blood pressure) can be stably and accurately calculated.

In addition, since this sphygmomanometer is a type that presses the wrist as a measurement target site, it is expected that a degree of hindering the sleep of the subject is smaller than a type that presses the upper arm (Imai et al., "Development and evaluation of a home nocturnal blood pressure monitoring system using a wrist-cuff device", Blood Pressure Monitoring 2018, 23, P318-326). Therefore, this sphygmomanometer is suitable for the nighttime (sleep) blood pressure measurement.

The sphygmomanometer according to one embodiment further comprises a second switching unit that, when a blood pressure measurement instruction is input by interruption by the measurement instruction input unit separately from the predetermined schedule in the nighttime blood pressure measurement mode, switches and sets the algorithm for the blood pressure calculation by the oscillometric method from the algorithm for the supine position to the algorithm for the sitting position for blood pressure measurement according to the blood pressure measurement instruction of the interruption.

Even while the sphygmomanometer is in the nighttime blood pressure measurement mode, the user may give an instruction to measure a blood pressure by interrupting, for example, by pressing a measurement switch provided in the sphygmomanometer, separately from the predetermined schedule. At this time, the subject is expected to be in a sitting position rather than a supine position. For this reason, when the blood pressure measurement according to the blood pressure measurement instruction is performed, if a blood pressure value is calculated as it is using the algorithm for the supine position, there arises a problem that the measurement accuracy is not good. Therefore, in the sphygmomanometer according to this embodiment, when the blood pressure measurement instruction is input by the interruption by the measurement instruction input unit separately from the predetermined schedule in the nighttime blood pressure measurement mode, the second switching unit switches and sets the algorithm for the blood pressure calculation by the oscillometric method from the algorithm for the supine position to the algorithm for the sitting position in order to measure a blood pressure according to the blood pressure measurement instruction of the interruption. In this state, in order to perform the blood pressure measurement according to the blood pressure measurement instruction of the interruption, the measurement target site is temporarily compressed by the blood pressure measuring cuff. When the blood pressure measuring cuff is in the pressurization process or the depressurization process, the blood pressure calculation unit calculates a blood pressure value using an algorithm (at this point, the algorithm for the sitting position) currently set for the blood pressure calculation by the oscillometric method based on a pressure of the blood pressure measuring cuff. Even in the nighttime blood pressure measurement mode, when the blood pressure measurement instruction is input by interruption by the measurement instruction input unit, as described above, the subject is expected to be in the sitting position rather than the supine position. Therefore, by using the algorithm for the sitting position, the blood pressure values (maximum blood pressure and minimum blood pressure) can be stably and accurately calculated. Therefore, according to the sphygmomanometer of this embodiment, the blood pressure value can be stably and accurately calculated when performing the blood pressure measurement according to the interruption blood pressure measurement instruction separately from the predetermined schedule in the nighttime blood pressure measurement mode.

The sphygmomanometer according to one embodiment further comprises a third switching unit that switches and sets the algorithm for the blood pressure calculation by the oscillometric method from the algorithm for the sitting position to the algorithm for the supine position as long as the blood pressure measurement is still scheduled by the schedule when the blood pressure measurement according to the blood pressure measurement instruction of the interruption is completed.

In the sphygmomanometer according to this embodiment, when the blood pressure measurement according to the blood pressure measurement instruction is completed, the third switching unit switches and sets the algorithm for the blood pressure calculation by the oscillometric method from the algorithm for the sifting position to the algorithm for the supine position as long as the blood pressure measurement is still scheduled by the schedule. Therefore, after the blood pressure measurement according to the interruption blood pressure measurement instruction is completed, the blood pressure measurement is automatically started according to the schedule. That is, the measurement target site is temporarily pressed by the blood pressure measuring cuff according to the schedule. When the blood pressure measuring cuff is in the pressurization process or the depressurization process, the blood pressure calculation unit calculates a blood pressure value using an algorithm (at this point, the algorithm for the supine position) currently set for the blood pressure calculation by the oscillometric method based on a pressure of the blood pressure measuring cuff. In the nighttime blood pressure measurement mode, as described above, the subject is usually expected to be in the supine position. Therefore, after the blood pressure measurement according to the blood pressure measurement instruction of the interruption is completed, the blood pressure values (maximum blood pressure and minimum blood pressure) can be stably and accurately calculated by using the algorithm for the supine position.

The sphygmomanometer according to one embodiment further comprises a fourth switching unit that switches and sets the algorithm for the blood pressure calculation by the oscillometric method from the algorithm for the supine position to the algorithm for the sitting position when all blood pressure measurements specified in the schedule are completed.

In the sphygmomanometer according to this embodiment, when all the blood pressure measurements specified in the schedule are completed, the fourth switching unit switches and sets the algorithm for the blood pressure calculation by the oscillometric method from the algorithm for the supine position to the algorithm for the sitting position. Therefore, for example, when starting the normal blood pressure measurement mode by default after the end of the nighttime blood pressure measurement mode, the blood pressure calculation unit can calculate a blood pressure value using the algorithm for the sitting position for the blood pressure calculation by the oscillometric method. Therefore, the blood pressure calculation in the normal blood pressure measurement mode can be correctly executed.

The sphygmomanometer according to one embodiment further comprises
 a main body provided integrally with the blood pressure measuring cuff,
 wherein each of the measurement instruction input unit and the mode operation unit includes a switch provided on an outer surface of the main body, and
 the main body is equipped with the algorithm storage unit, each switching unit, a pressure control unit that controls a pressure of the blood pressure measuring cuff, and the blood pressure calculation unit.

Here, the "pressure control unit" includes, for example, a pump that supplies a pressurizing fluid to the blood pressure measuring cuff, a valve that exhausts the fluid from the blood pressure measuring cuff, and elements that drive and control these pumps, valves, and the like.

The sphygmomanometer of this embodiment can be integrally and compactly configured as a wrist-type sphygmomanometer. Therefore, handling by the user is convenient.

In another aspect, a blood pressure calculation method according to the present disclosure is a blood pressure calculation method for a sphygmomanometer that temporarily presses a wrist as a measurement target site with a blood pressure measuring cuff, and performs blood pressure measurement by an oscillometric method, wherein the sphygmomanometer includes:
a measurement instruction input unit configured to input a blood pressure measurement instruction;
a mode operation unit configured to input an instruction to switch a mode between a normal blood pressure measurement mode in which the blood pressure measurement is performed according to the blood pressure measurement instruction input by the measurement instruction input unit and a nighttime blood pressure measurement mode in which the blood pressure measurement is automatically started according to a predetermined schedule; and
an algorithm storage unit that stores an algorithm for a sitting position and an algorithm for a supine position as an algorithm for blood pressure calculation by an oscillometric method,
the blood pressure calculation method comprising:
switching and setting the algorithm for the blood pressure calculation by the oscillometric method from the algorithm for the sitting position to the algorithm for the supine position when being switched by the mode operation unit from the normal blood pressure measurement mode to the nighttime blood pressure measurement mode; and
calculating a blood pressure value using an algorithm currently set for the blood pressure calculation by the oscillometric method based on a pressure of the blood pressure measuring cuff when the blood pressure measuring cuff is in a pressurization process or a depressurization process.

According to this blood pressure calculation method, the blood pressure value can be stably and accurately calculated when the blood pressure measurement according to the interruption blood pressure measurement instruction is performed separately from the predetermined schedule in the nighttime blood pressure measurement mode.

In yet another aspect, a computer-readable recording medium according to the present disclosure is a computer-readable recording medium non-transitorily storing a program for causing a computer to execute the above blood pressure calculation method.

By making a computer read the program stored in the computer-readable recording medium according to the present disclosure and causing a computer to execute the program, the blood pressure calculation method can be implemented.

As is clear from the above, according to the sphygmomanometer and the blood pressure calculation method of the present disclosure, the blood pressure value can be stably and accurately calculated in the sphygmomanometer having the normal blood pressure measurement mode and the nighttime (sleep) blood pressure measurement mode. Furthermore, according to the program stored in the computer-readable recording medium of the present disclosure, it is possible to cause a computer to execute such a blood pressure calculation method.

The above embodiments are illustrative, and are modifiable in a variety of ways without departing from the scope of this invention. It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. A sphygmomanometer that temporarily presses a wrist as a measurement target site with a blood pressure measuring cuff, and performs blood pressure measurement by an oscillometric method, the sphygmomanometer comprising:
a first switch configured to input a blood pressure measurement instruction;
a second switch configured to input an instruction to switch a mode between a normal blood pressure measurement mode in which the blood pressure measurement is performed according to the blood pressure measurement instruction input by the first switch and a nighttime blood pressure measurement mode in which the blood pressure measurement is automatically started according to a predetermined schedule;
a memory configured to store an algorithm for a sitting position and an algorithm for a supine position as an algorithm for blood pressure calculation by the oscillometric method; and
a programmed processor, wherein
the programmed processor is configured to act as:
a first switching unit to switch and set the algorithm for the blood pressure calculation by the oscillometric method from the algorithm for the sitting position to the algorithm for the supine position when being switched by the second switch from the normal blood pressure measurement mode to the nighttime blood pressure measurement mode;
a second switching unit to switch and set, when a blood pressure measurement instruction is input by interruption by the first switch separately from the predetermined schedule in the nighttime blood pressure measurement mode, the algorithm for the blood pressure calculation by the oscillometric method from the algorithm for the supine position to the algorithm for the sitting position for blood pressure measurement according to the blood pressure measurement instruction of the interruption; and
a blood pressure calculation unit to calculate a blood pressure value using an algorithm currently set for the blood pressure calculation by the oscillometric method based on a pressure of the blood pressure measuring cuff when the blood pressure measuring cuff is in a pressurization process or a depressurization process.

2. The sphygmomanometer according to claim 1, wherein the programmed processor is configured to further act as a third switching unit to switch and set the algorithm for the blood pressure calculation by the oscillometric method from the algorithm for the sitting position to the algorithm for the supine position as long as the blood pressure measurement is still scheduled by the schedule when the blood pressure measurement according to the blood pressure measurement instruction of the interruption is completed.

3. The sphygmomanometer according to claim 1, wherein the programmed processor is configured to further act as a fourth switching unit to switch and set the algorithm for the blood pressure calculation by the oscillometric method from the algorithm for the supine position to the algorithm for the sitting position when all blood pressure measurements specified in the schedule are completed.

4. The sphygmomanometer according to claim 1, wherein a main body provided integrally with the blood pressure measuring cuff,
wherein the first and second switches are on an outer surface of the main body, and
the main body is equipped with the memory, the programmed processor, and a pressure controller that controls a pressure of the blood pressure measuring cuff.

5. A blood pressure calculation method for a sphygmomanometer that temporarily presses a wrist as a measurement target site with a blood pressure measuring cuff, and performs blood pressure measurement by an oscillometric method, wherein the sphygmomanometer includes:
   a first switch configured to input a blood pressure measurement instruction;
   a second switch configured to input an instruction to switch a mode between a normal blood pressure measurement mode in which the blood pressure measurement is performed according to the blood pressure measurement instruction input by the first switch and a nighttime blood pressure measurement mode in which the blood pressure measurement is automatically started according to a predetermined schedule;
   a memory configured to store an algorithm for a sitting position and an algorithm for a supine position as an algorithm for blood pressure calculation by an oscillometric method; and
   a programmed processor,
   the blood pressure calculation method comprising:
   switching and setting, by the programmed processor, the algorithm for the blood pressure calculation by the oscillometric method from the algorithm for the sitting position to the algorithm for the supine position when being switched by the second switch from the normal blood pressure measurement mode to the nighttime blood pressure measurement mode;
   when a blood pressure measurement instruction is input by interruption by the first switch separately from the predetermined schedule in the nighttime blood pressure measurement mode, switching and setting, by the programmed processor, the algorithm for the blood pressure calculation by the oscillometric method from the algorithm for the supine position to the algorithm for the sitting position for blood pressure measurement according to the blood pressure measurement instruction of the interruption; and
   calculating, by the programmed processor, a blood pressure value using an algorithm currently set for the blood pressure calculation by the oscillometric method based on a pressure of the blood pressure measuring cuff when the blood pressure measuring cuff is in a pressurization process or a depressurization process.

6. A computer-readable recording medium non-transitorily storing a program for causing a computer to execute the blood pressure calculation method according to claim 5.

7. A sphygmomanometer that temporarily presses a wrist as a measurement target site with a blood pressure measuring cuff, and performs blood pressure measurement by an oscillometric method, the sphygmomanometer comprising:
   a first switch configured to input a blood pressure measurement instruction;
   a second switch configured to input an instruction to switch a mode between a normal blood pressure measurement mode in which the blood pressure measurement is performed according to the blood pressure measurement instruction input by the first switch and a nighttime blood pressure measurement mode in which the blood pressure measurement is automatically started according to a predetermined schedule;
   a memory configured to store an algorithm for a sitting position and an algorithm for a supine position as an algorithm for blood pressure calculation by the oscillometric method; and
   a programmed processor, wherein
   the programmed processor is configured to act as:
      a first switching unit to switch and set the algorithm for the blood pressure calculation by the oscillometric method from the algorithm for the sitting position to the algorithm for the supine position when being switched by the second switch from the normal blood pressure measurement mode to the nighttime blood pressure measurement mode;
      a blood pressure calculation unit to calculate a blood pressure value using an algorithm currently set for the blood pressure calculation by the oscillometric method based on a pressure of the blood pressure measuring cuff when the blood pressure measuring cuff is in a pressurization process or a depressurization process; and
      an additional switching unit to switch and set the algorithm for the blood pressure calculation by the oscillometric method from the algorithm for the supine position to the algorithm for the sitting position when all blood pressure measurements specified in the schedule are completed.

* * * * *